(12) United States Patent
Hong et al.

(10) Patent No.: US 9,576,366 B2
(45) Date of Patent: Feb. 21, 2017

(54) TRACKING SYSTEM AND TRACKING METHOD USING THE SAME

(71) Applicants: KOH YOUNG TECHNOLOGY INC., Seoul (KR); KYUNGPOOK NATIONAL UNIVERSITY INDUSTRY-ACADEMIC COOPERATION FOUNDATION, Daegu (KR)

(72) Inventors: Jong-Kyu Hong, Gwangju-si (KR); Hyun-Ki Lee, Daegu (KR); Min-Young Kim, Daegu (KR); Jae-Heon Chung, Gwangmyeong-si (KR)

(73) Assignees: KOH YOUNG TECHNOLOGY INC., Seoul (KR); KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 10 days.

(21) Appl. No.: 14/370,549

(22) PCT Filed: Jan. 7, 2014

(86) PCT No.: PCT/KR2014/000131
§ 371 (c)(1),
(2) Date: Jul. 3, 2014

(87) PCT Pub. No.: WO2014/109520
PCT Pub. Date: Jul. 17, 2014

(65) Prior Publication Data
US 2015/0302590 A1 Oct. 22, 2015

(30) Foreign Application Priority Data
Jan. 10, 2013 (KR) ........................ 10-2013-0002841

(51) Int. Cl.
| | |
|---|---|
| H04N 13/00 | (2006.01) |
| H04N 13/02 | (2006.01) |
| G06T 7/00 | (2006.01) |

(52) U.S. Cl.
CPC ............. *G06T 7/0044* (2013.01); *A61B 34/20* (2016.02); *A61B 34/30* (2016.02); *A61B 90/39* (2016.02);
(Continued)

(58) Field of Classification Search
USPC ..................................... 348/4–512
See application file for complete search history.

(56) References Cited

U.S. PATENT DOCUMENTS

| | | | |
|---|---|---|---|
| 5,394,875 | A | 3/1995 | Lewis et al. |
| 5,923,417 | A | 7/1999 | Leis |

(Continued)

FOREIGN PATENT DOCUMENTS

| | | |
|---|---|---|
| CN | 101049229 | 10/2007 |
| CN | 101379412 | 3/2009 |

(Continued)

OTHER PUBLICATIONS

Written Opinion of the International Searching Authority for International Application No. PCT/KR2014/000131, dated Apr. 30, 2014.

*Primary Examiner* — Nigar Chowdhury
(74) *Attorney, Agent, or Firm* — Kile Park Reed & Houtteman PLLC (57) ABSTRACT

A tracking system and method using the same is disclosed which is capable of minimizing a restriction of surgical space by achieving a lightweight of the system as well as a reduction of a manufacturing cost through calculating a three-dimensional coordinates of each of makers using one image forming unit. In the tracking system and method using (Continued)

the same, lights emitted from the markers are transferred to one image forming unit through two optical paths, an image sensor of the image forming unit forms two images (direct image and reflection image) of the two optical paths of the markers, and therefore, the system and method using the same has an effect of reducing a manufacturing cost of the tracking system with small and lightweight, and relatively low restriction of surgical space comparing with conventional tracking system since it is possible to calculate a spatial position and direction of the markers attached on a target by using one image forming unit.

9 Claims, 6 Drawing Sheets (52) U.S. Cl.
CPC ...... *H04N 13/0271* (2013.01); *H04N 13/0296* (2013.01); *A61B 2034/2055* (2016.02); *A61B 2034/2057* (2016.02); *A61B 2090/363* (2016.02); *A61B 2090/3937* (2016.02); *A61B 2090/3945* (2016.02); *A61B 2090/3983* (2016.02); *G06T 2207/10028* (2013.01); *G06T 2207/30004* (2013.01); *G06T 2207/30204* (2013.01)

(56) References Cited

U.S. PATENT DOCUMENTS

| | | | |
|---|---|---|---|
| 2002/0130977 A1* | 9/2002 | Hibi | H04N 9/3114 348/744 |
| 2003/0176783 A1 | 9/2003 | Hu | |
| 2003/0209096 A1 | 11/2003 | Pandey et al. | |
| 2004/0160594 A1* | 8/2004 | Suphellen | G01B 11/002 356/4.01 |
| 2004/0223139 A1* | 11/2004 | Vogel | G01S 5/163 356/141.1 |
| 2005/0015005 A1 | 1/2005 | Kockro | |
| 2006/0082789 A1* | 4/2006 | Goldbach | G01S 5/16 356/620 |
| 2006/0192921 A1* | 8/2006 | Loesel | A61F 9/008 351/219 |
| 2006/0240568 A1* | 10/2006 | Petruno | G01N 21/8483 436/514 |
| 2007/0183041 A1 | 8/2007 | McCloy et al. | |
| 2007/0236661 A1 | 10/2007 | Fukuma et al. | |
| 2009/0009759 A1* | 1/2009 | Backman | A61B 1/00096 356/303 |
| 2009/0131921 A1* | 5/2009 | Kurtz | A61F 9/00825 606/4 |
| 2009/0137952 A1* | 5/2009 | Ramamurthy | A61B 5/06 604/95.01 |
| 2010/0188401 A1* | 7/2010 | Gordon | G06T 7/2033 345/420 |
| 2011/0211066 A1 | 9/2011 | Fujiki | |
| 2012/0330154 A1 | 12/2012 | Beasley et al. | |

FOREIGN PATENT DOCUMENTS

| | | |
|---|---|---|
| EP | 2 233 099 | 9/2010 |
| JP | 2001-506762 | 5/2001 |
| JP | 2006-284442 | 10/2006 |
| JP | 2007-130398 | 5/2007 |
| JP | 2009-294048 | 12/2009 |
| JP | 2011-179910 | 9/2011 |
| KR | 10-0835186 | 6/2008 |
| KR | 10-2011-0118640 | 10/2011 |
| WO | 02/02028 | 1/2002 |

* cited by examiner

TRACKING SYSTEM AND TRACKING METHOD USING THE SAME

TECHNICAL FIELD

Exemplary embodiments of the present invention relate to a tracking system and tracking method using the same. More particularly, exemplary embodiments of the present invention relate to a tracking system and tracking method using the same for surgery capable of detecting a spatial and a direction information of a target by tracking coordinates of markers attached on the target, in which the target are markers attached on a patient or a surgical instrument.

BACKGROUND ART

Recently, a robot surgery have been studied and introduced to reduce pain of patients and to recover faster in an endoscopic surgery or an otolaryngology surgery (ENT surgery).

In such a robot surgery, in order to minimize a risk of the surgery and to operate the surgery more precisely, a navigation system is used to navigate to an exact lesion of a patient by tracking and detecting a spatial position and a direction of a target such as lesion portion or surgical instrument.

The navigation system described above includes a tracking system which is capable of tracking and detecting a spatial position and direction of a target such as lesion or surgical instrument.

The tracking system described above includes a plurality of markers attached on a lesion or a surgical instrument, a first and second image forming units to form images of lights emitted from the markers, and a processor calculating three-dimensional coordinates of the markers which are connected to the first and second image forming units and calculating a spatial position and a direction of the target by comparing pre-stored information of straight lines connecting the markers adjacent to each other and angle information formed by a pair of straight lines adjacent to each other to the three-dimensional coordinates of the markers.

Herein, in order to calculate the three-dimensional coordinates of the markers, conventionally, two detectors are required to calculate the three-dimensional coordinates of each markers through a processor, a trigonometry is used in an assumption that a coordinate of marker which is emitted from one marker and formed image in a first image forming unit and a coordinate of marker which is emitted from one marker and formed image in a second image forming unit are identical.

Conventional tracking system requires two image forming units to form images of lights which are emitted from each markers positioned different to each other, a manufacturing cost increases as well as a whole size also increases, therefore, a restriction of surgical space is generated.

DISCLOSURE

Technical Problem

Therefore, the technical problem of the present invention is to provide a tracking system and method using the same capable of reducing a manufacturing cost as well as minimizing a restriction of a surgical space by achieving compact of a system through calculating three-dimensional coordinates of each of markers by using only one image forming unit.

Technical Solution

In one embodiment of the present invention, a tracking system includes at least three markers which are attached on a target to emit lights or reflect lights emitted from a light source, a reflector which reflects light emitted from the makers or reflected light from the markers, an image forming unit which forms a direct image by directly receiving lights emitted from the markers and, at the same time, forming a reflection image by receiving lights reflected from the reflector after being emitted from markers, and a processor which calculates three-dimensional coordinates of each markers by using the direct image and the reflection image formed on the image forming unit, compares the three-dimensional coordinates of the markers to pre-stored geometric information of the markers which are adjacent to each other, and calculates a spatial position and a direction of the target.

In one embodiment, the reflector may be a mirror to form a reflection image by reflecting the emitted light from the markers to the image forming unit.

In one embodiment, the reflector is positioned on the same optical path as the image forming unit, changes at least one of a position, an angle and a shape of a reflection surface under the control of the processor, and changes an image forming position of the reflection image.

In one embodiment, the image forming unit may be a camera capable of forming image by receiving a direct light emitted from the markers and a reflected light reflected by the reflector.

Meanwhile, geometric information of the markers may be length information coupling markers adjacent to each other and angle information formed by a pair of straight lines adjacent to each other.

In one embodiment of the present invention, a tracking method includes forming a direct image on an image forming units by directly receiving lights emitted from at least three markers which are attached on a target and, at the same time, forming a reflection image on the image forming unit by receiving lights which are reflected from the reflector, the reflector is installed on a specific position and reflects lights emitted from the markers, calculating three-dimensional coordinates of each markers by using the direct image and the reflection image of the markers formed on the image forming unit through the processor, and calculating a spatial position and a direction of the target by comparing the three-dimensional coordinates of the each markers to pre-stored geometric information of markers which are adjacent to each other.

Herein, the geometric information of the markers may be length information coupling markers which are adjacent to each other and angle information formed by a pair of straight lines adjacent to each other.

In one embodiment, the process of calculating the three-dimensional coordinates of the marker may further include calculating two-dimensional coordinates of the direct image and reflection image which are formed on the image forming unit through the processor, and calculating the three-dimensional coordinates of the markers by using the two-dimensional coordinates of the direct image and reflection image of the markers.

Advantageous Effects

Thus, according to an embodiment of the present invention, in a tracking system and tracking method using the same, lights emitted from each of the markers are directly flowed to an image forming unit and, at the same time, lights reflected by the reflector are directly flowed to the image forming units. In other words, lights emitted from each of the markers are flowed to the image forming unit through two paths (first path: marker→image forming unit, second path: marker→reflector→image forming unit), an image sensor of the image forming unit forms images of the markers according to the two paths, and therefore, it is possible to calculate a spatial position and a direction of the markers attached on the target by using only one image forming unit.

Therefore, there is an effect of reducing manufacturing cost of the tracking system, making small and lightweight, and relatively low restriction of a surgical space compared to the conventional tracking system.

MODE FOR INVENTION

The present invention is described more fully hereinafter with reference to the accompanying drawings, in which example embodiments of the present invention are shown. The present invention may, however, be embodied in many different forms and should not be construed as limited to the example embodiments set forth herein. Rather, these example embodiments are provided so that this disclosure will be thorough and complete, and will fully convey the scope of the present invention to those skilled in the art. In the drawings, the sizes and relative sizes of layers and regions may be exaggerated for clarity.

It will be understood that, although the terms first, second, third etc. may be used herein to describe various elements, components, regions, layers and/or sections, these elements, components, and/or sections should not be limited by these terms. These terms are only used to distinguish one element, component, region, layer or section from another region, layer or section. Thus, a first element, component, or section discussed below could be termed a second element, component, or section without departing from the teachings of the present invention.

The terminology used herein is for the purpose of describing particular example embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, with reference to the drawings, preferred embodiments of the present invention will be described in detail.

In a tracking system and method using the same according to an embodiment of the present invention, at least three markers are attached and three-dimensional coordinates of the markers are calculated, geometric information of markers adjacent to each, which are pre-stored in a processor, are compared to the three-dimensional coordinates of the markers through the processor, and therefore, it is capable of calculating a spatial position and a direction of a target such as a lesion or surgical instrument. Detailed description is explained with referencing the figures.

Figure 1:
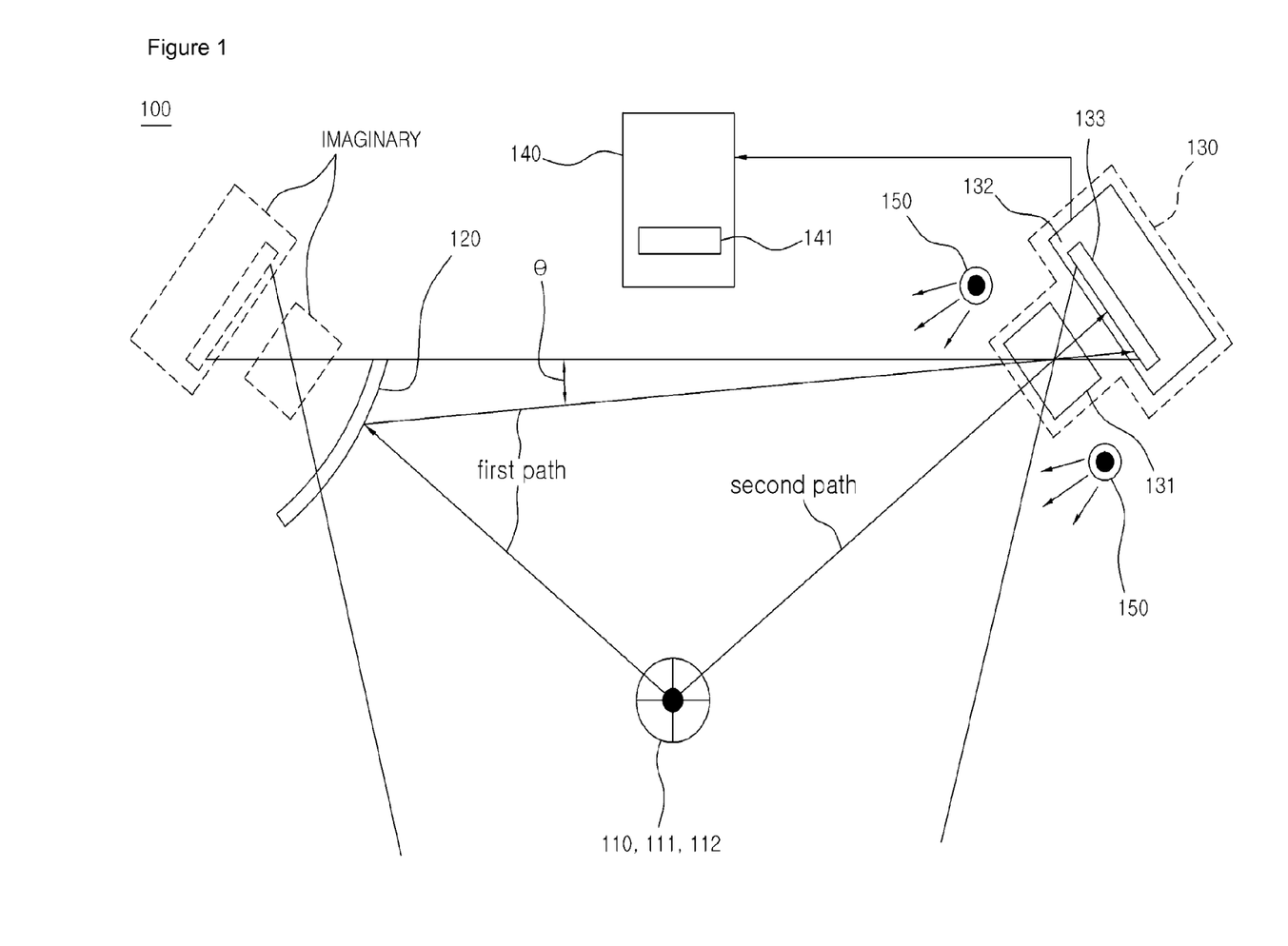
FIG. 1 is a schematic diagram of a tracking system according to an embodiment of the present invention.
Figure 2:
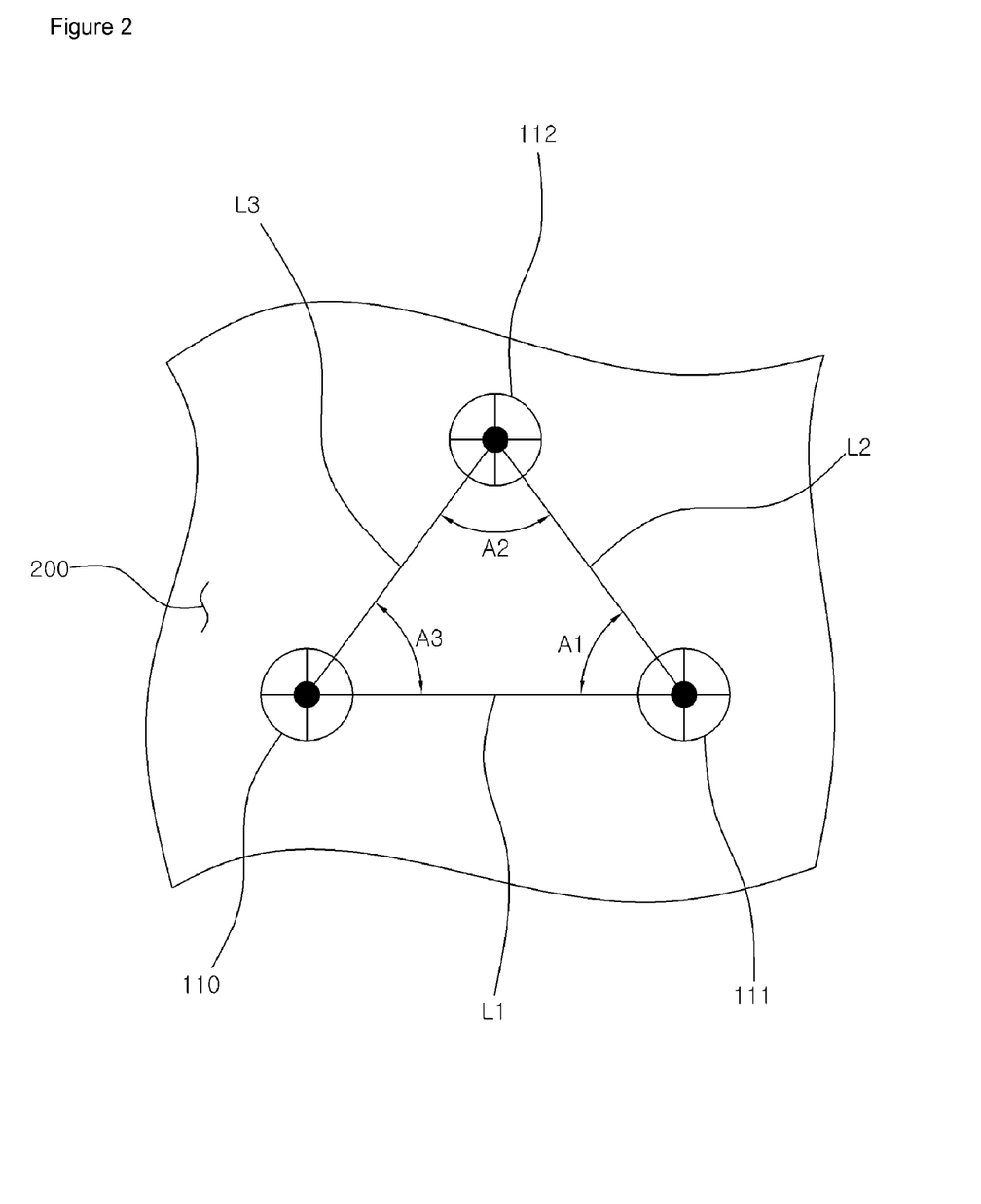
FIG. 2 is an example diagram of markers attached on a target.
Figure 3:
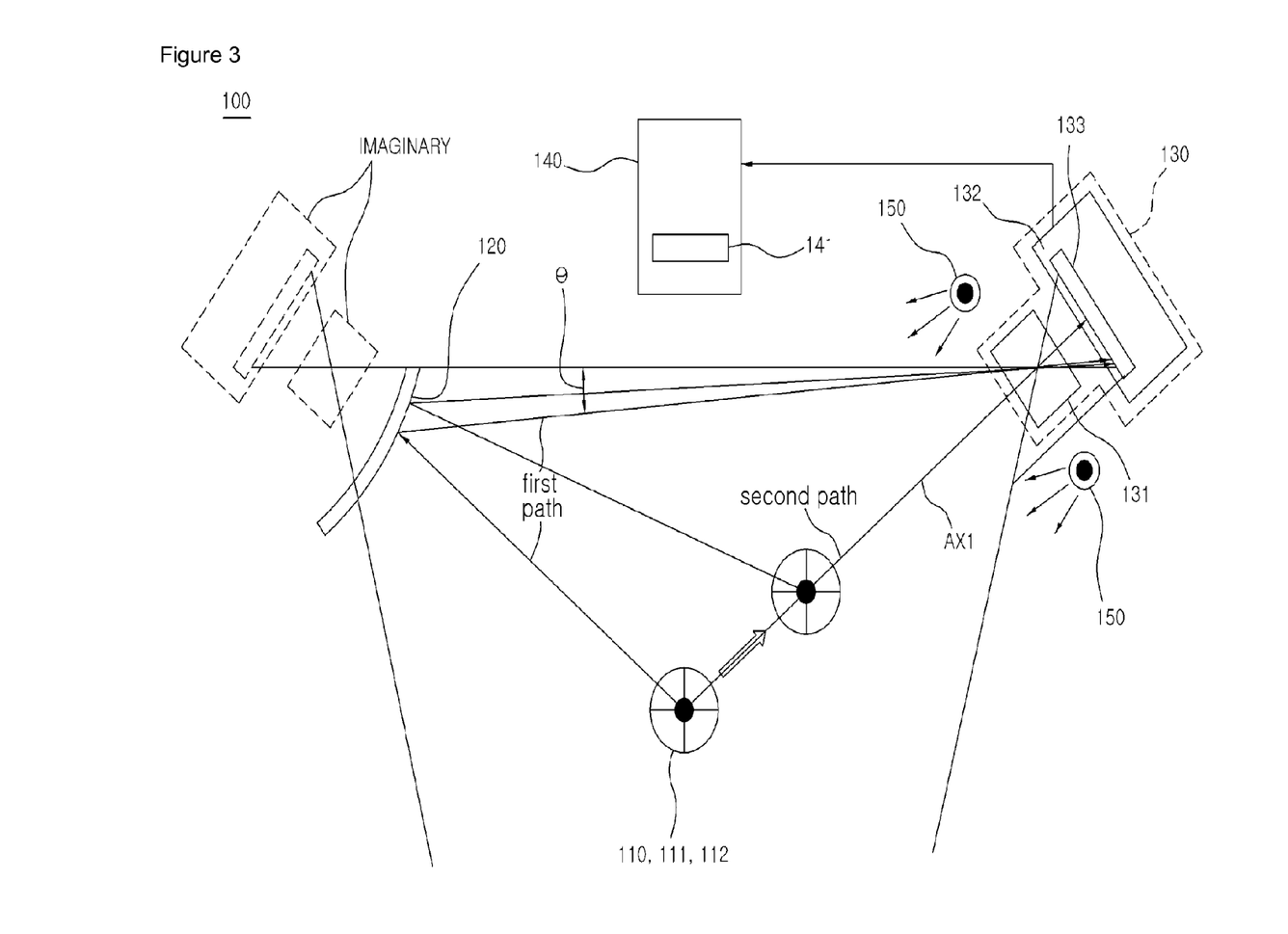
FIG. 3 is an example diagram explaining a position change of a reflection image when a position of the marker is changed on a same optical path as a lens.

FIG. 1 is a schematic diagram of a tracking system according to an embodiment of the present invention, FIG. 2 is an example diagram of markers attached on a target, and FIG. 3 is an example diagram explaining a position change of a reflection image when a position of the marker is changed on a same optical path as a lens.

For the convenience of description, a marker is shown in FIGS. 1 and 3, however, in a tracking system according to an embodiment of the present invention, at least three markers 110 111 and 112 are attached on a target 200 such as a lesion or a surgical instrument.

Referring to FIGS. 1 to 3, a tracking system according to an embodiment of the present invention includes at least three markers 110 111 and 112, a reflector 120, an image forming unit 130, and a processor 140.

At least three markers 110 111 and 112 are attached on the target 200 such as a lesion or a surgical instrument. Herein, the at least three markers 110 111 and 112 are separated to each other in a predetermined interval, the markers are attached on the target 200 such as a lesion or a surgical instrument to form specific angles A1 A2 and A3 which are formed by a pair of straight lines of the adjacent markers, in which the straight lines L1 L2 and L3 virtually connect the adjacent markers 110 111 and 112.

Herein, geometric information between the markers 110 111 and 112 which are adjacent to each other, in other words, length information of straight lines L1 L2 and L3 which connect the markers 112 which are adjacent to each other and angle information A1 A2 and A3 formed by a pair of the straight lines, are stored in a memory 141 of the processor 140.

For example, the markers 110 111 and 112 may be attached on the target 200 such as a lesion and a surgical instrument in a triangle shape, and straight line information L1 L2 and L3 forming sides of the triangle in which the markers are used as vertices and angle information A1 A2 and A3 in which angles are formed by a pair of straight lines coupling each of the markers 110 111 and 112 may be pre-stored in the memory 141 of the processor 140.

Meanwhile, the markers 110 111 and 112 may be an active markers which emit lights by itself. As described above, when an active marker is used for the markers 110 111 and 112, a light source is not needed.

Alternatively, the markers 110 111 and 112 may be passive markers which reflect a light emitted from at least one light source 150. As described above, when a passive markers are used as the markers 110 111 and 112, at least one light source 150 may be arranged close to the image forming unit 130. For example, a pair of light source 150 may be arranged on both sides of the image forming unit 130.

The reflector 120 reflects lights emitted from the markers 110 111 and 112 or lights reflected by the markers 110 111 and 112. For example, the reflector 120 reflects lights emitted from the markers 110 111 and 112 or re-reflects lights reflected by the maker 110 111 and 112 which are emitted from the light source 150.

Herein, the reflector may be a mirror which reflects lights emitted from the markers 110 111 and 112 to form an image of a reflection image on the image forming unit 130. For example, the reflector 120 may be a spherical mirror. Thus, when a spherical mirror is used for the reflector 120, since a θ value is reduced when a marker changes its position on a same optical path AX1 as the image forming unit 130 as shown in FIG. 3, a position of a marker is calculated based on the θ value.

Meanwhile, by changing an installation position, an installation angle, or a shape of a reflection surface, the reflector may change an image formation position of a reflection image formed on the image forming unit 130. In other words, it is possible to vary a measurement range by changing an installation position, an installation angle, or a shape of a reflection surface.

Herein, changing the position, the angle, or the shape of the reflection surface of the reflector may be controlled by the processor 140 which is interlocked in a wired/wireless network. Thus, it is capable of changing an optical path as the reflection image by moving the reflector 120 when the optical path is screened by a stand of a surgical robot, an arm, a doctor or a nurse, etc.

Or, when the reflection image is not received in a certain period of time after the processor directly receives an image of the markers 110 111 and 112, then, the processor decides that there is an obstacle in an optical path, and in such a case, the processor may send a control information to the reflector 120 such that the control information may move the reflector 120 to pre-stored value by controlling at least one of the installation position, the angle, the shape of the reflection surface of the reflector 120.

The spatial position and the direction of the reflector 120 and the changed spatial position and the direction of the reflector 120 may be stored in the memory 141 integrated in the processor 140.

The image forming unit 130 directly receives lights emitted from the markers 110 111 and 112 and forms an image and, at the same time, receives lights reflected from the reflector 120 which are emitted from the markers 110 111 112 and forms an image.

For example, the image forming unit 130 may be a camera which receives lights from the reflector 120 that are directly emitted from the markers 110 111 and 112, and forms images. In other words, the image forming unit 130 may include a lens 131 in which lights emitted from the markers 110 111 and 112 and lights reflected from the reflector 120 pass through a focal, a body portion 132 arranged on a back portion of the lens 131 in which an image sensor 133 is integrated, the image sensor forms images by receiving lights emitted from the markers 110 111 and 112 and lights reflected from the reflector 120.

The processor 140 calculates three-dimensional coordinates of the markers 110 111 and 112 using the direct image and the reflection image formed on the image forming unit 130, and is capable of calculating a spatial position and a direction of the target 200 such as a lesion or a surgical instrument by comparing the three-dimensional coordinates of the markers 110 111 and 112 with the pre-stored geometric information of the adjacent markers 110 111 and 112.

Herein, a memory 141 is integrated in the processor 140. Meanwhile, geometric information between the markers which are adjacent to each other, in other words, length information of straight lines L1 L2 and L3 which connect the marker adjacent to each other and angle information A1 A2 and A3 which are formed by the pair of straight lines coupling the markers 110 111 and 112 adjacent to each other may be pre-stored the memory 141 integrated in the processor 140.

Additionally, a spatial position and a direction of the reflector 120 may be pre-stored in the memory 141 integrated in the processor 140.

As described above, in the tracking system 100 according to an embodiment of the present invention, lights emitted from the markers 110 111 and 112 flow to the image forming unit 130 and a direct image is formed on the image forming unit 130, as well as, lights reflected from the reflector 120 in which the lights emitted from the markers 110 111 and 112 flow to the reflector 120 and flow to the image forming unit 130, and a reflection image is formed on the image forming units 130, and therefore, even though one image forming unit 130 is used, there is the same effect as using additional image forming unit as shown in a dotted line on the left side of the reflector 120 in FIGS. 1 and 3.

Referring to FIGS. 1-7, a tracking process of a spatial position and a direction of a target using a tracking system according to an embodiment of the present invention is described below.

Figure 4:
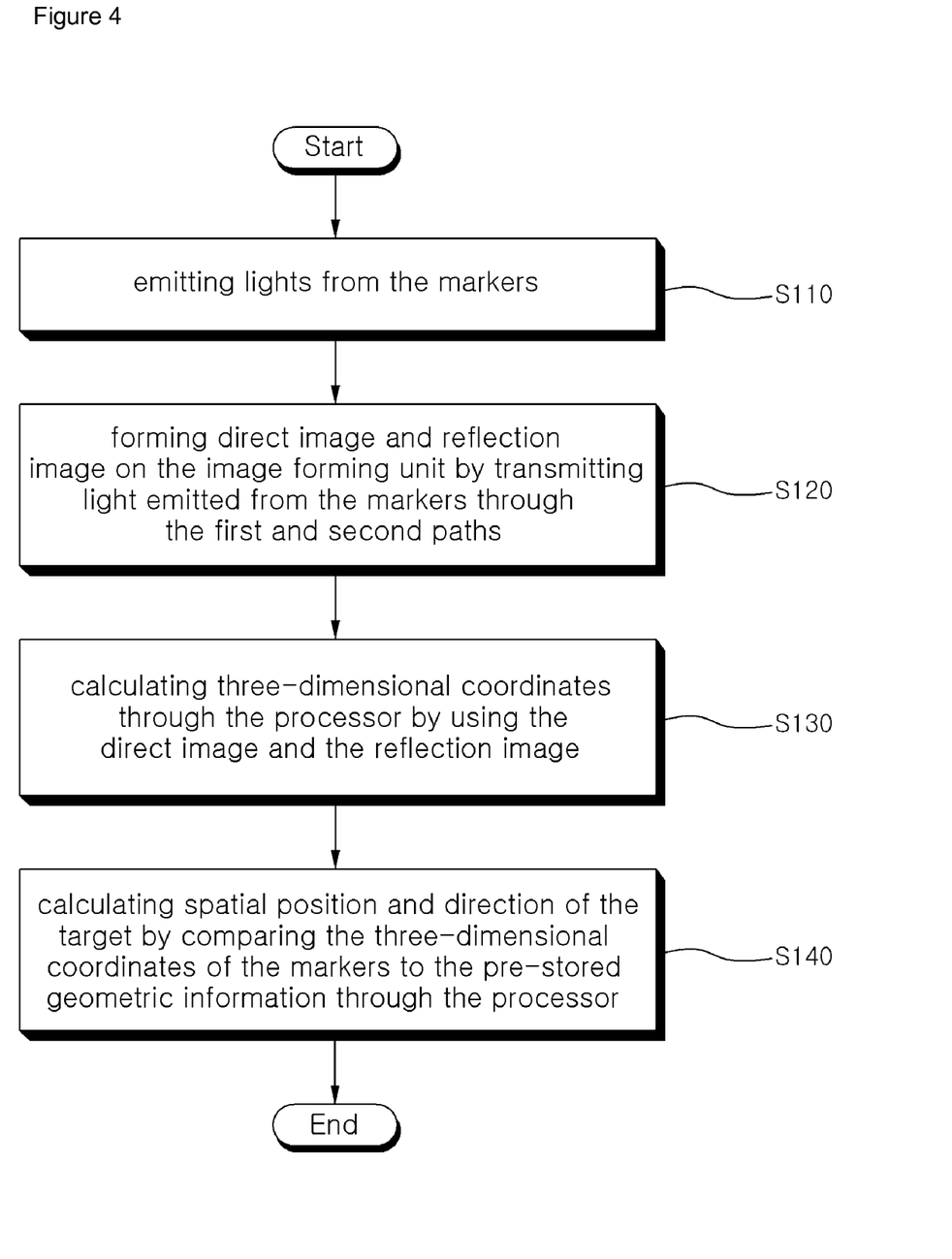
FIG. 4 is a block diagram explaining a tracking method according to an embodiment of the present invention.
Figure 5:
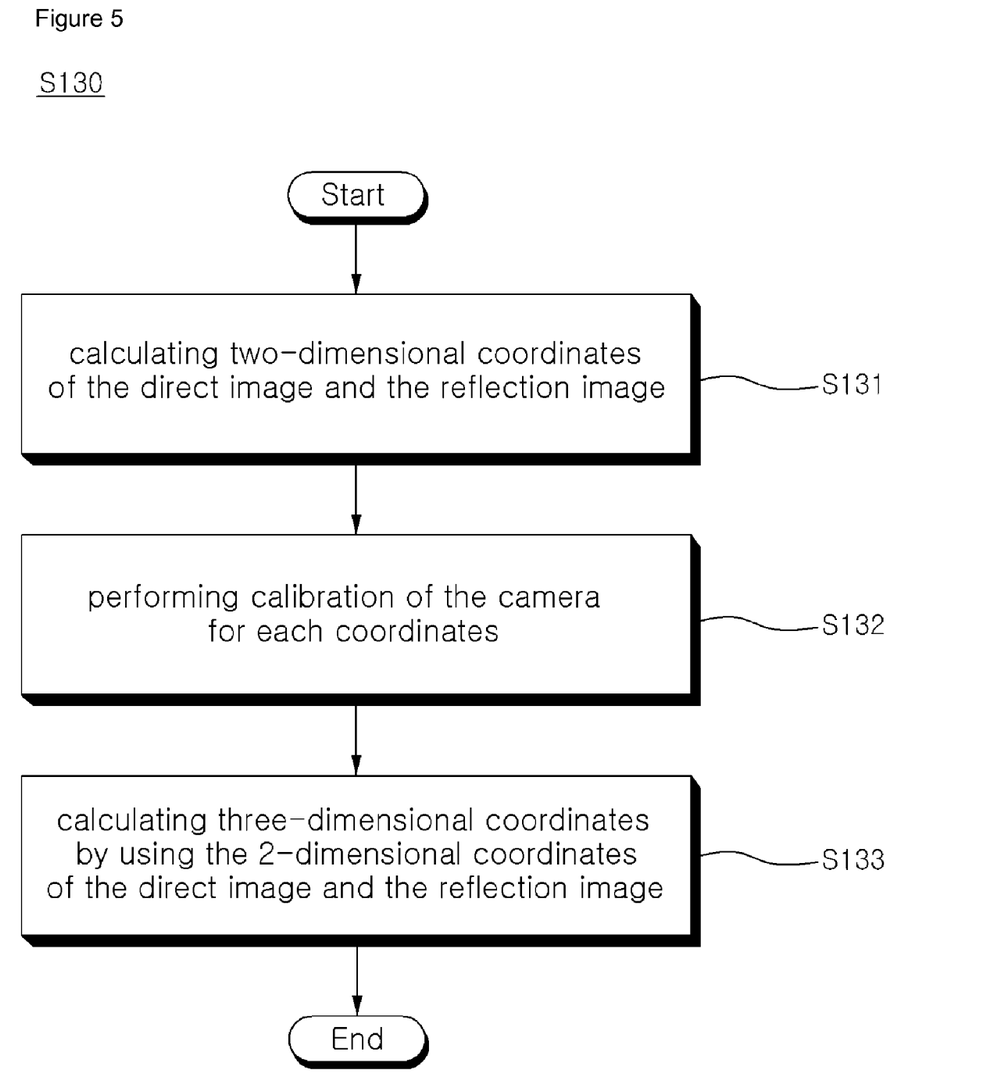
FIG. 5 is a block diagram explaining a method of calculating three-dimensional coordinates.
Figure 6:
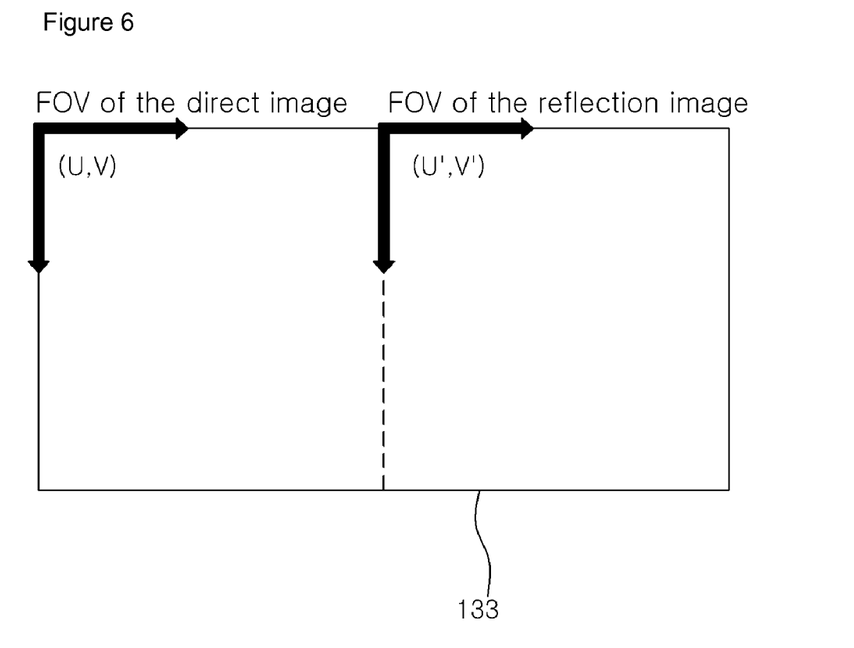
FIG. 6 is an example diagram of an image sensor of the image forming unit in which a coordinate of a direct image and coordinate of a reflection image is virtually divided.
Figure 7:
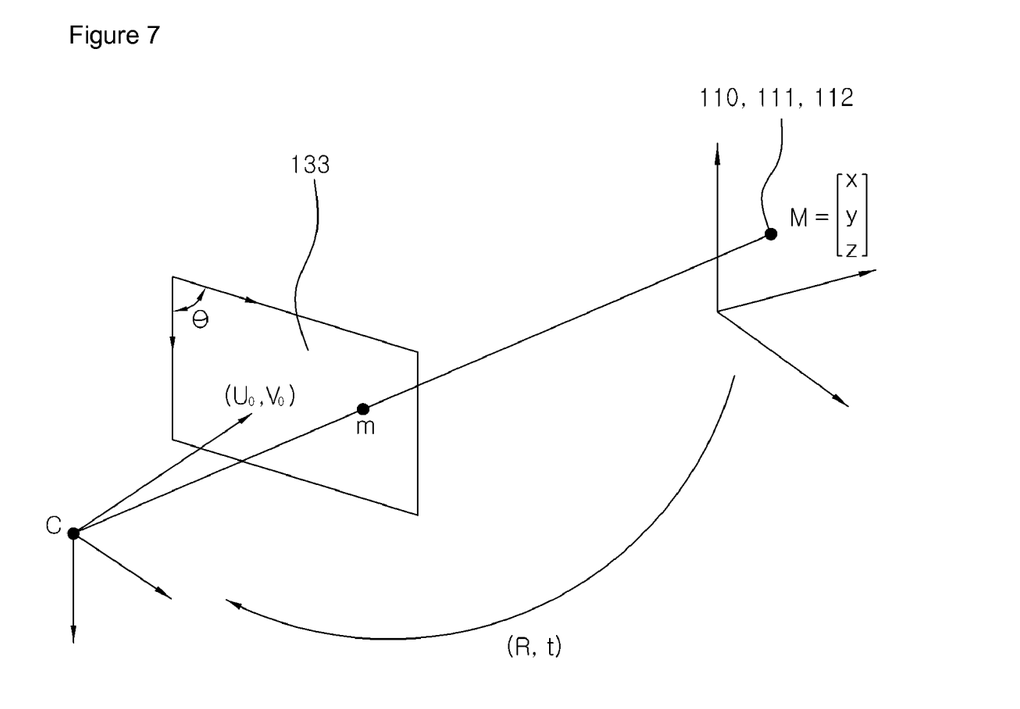
FIG. 7 is a diagram explaining a relationship between two-dimensional coordinates and three-dimensional coordinates of a real marker.

FIG. 4 is a block diagram explaining a tracking method according to an embodiment of the present invention, FIG. 5 is a block diagram explaining a method of calculating three-dimensional coordinates, FIG. 6 is an example diagram of an image sensor of the image forming unit in which a coordinate of a direct image and coordinate of a reflection image is virtually divided, and FIG. 7 is a diagram explaining a relationship between two-dimensional coordinates and three-dimensional coordinates of a real marker.

Referring to FIGS. 1-7, in order to track a spatial position and a direction of a target 200 using a tracking system according to an embodiment of the present invention, first, at least three markers 110 111 and 112 which are attached on the target 200 are activated making the markers 110 111 and 112 to emit light, or, at least one light source is activated to irradiated light toward the markers 110 111 and 112 which are attached on the target 200 such that the light is reflected and emitted by the markers 110 111 and 112 (S11).

In more detail, when at least three self-luminous markers 110 111 and 112 are attached on the target 200, the markers 110 111 and 112 are activated to emit lights. Alternatively, when at least three passive (non-self-luminous) markers 110 111 and 112 are attached on the target 200, at least one light source is activated to irradiated light toward the passive markers 110 111 and 112 which are attached on the target 200 such that the light is reflected and emitted by the passive markers 110 111 and 112.

Lights emitted from the at least three markers 110 111 and 112 are directly transferred to the image forming unit 130 and a direct image of each of the markers 110 111 and 112 are formed in the image forming unit 130, and at the same time, lights reflected from the reflector 120, in which the light emitted from the at least markers 110 111 and 112 are transferred to the reflector 120, are transferred to the image forming unit 130 and a reflection image of each of the markers 110 111 and 112 are formed in the image forming unit 130 (S120).

In other words, a direct image is formed on the image forming unit 130 by directly receiving lights emitted from at least three markers 110 111 and 112 which are attached on the target 200 and, at the same time, a reflection image is formed on the image forming unit 130 by receiving lights reflected from the reflector 120 in which the light emitted from the at least markers 110 111 and 112 are transferred to the reflector 120.

In more detail, lights emitted from the at least three markers 110 111 and 112 are directly transferred to the image forming unit 130 through a first optical path, pass a lens of the image forming unit 130, and make a direct image of the at least three markers 110 111 and 112 on an image sensor 133 integrated in the body portion 132 and, at the same time, lights emitted from the at least three markers 110 111 and 112 are reflected by the reflector 120 through a second optical path and transferred to the image forming unit 130, pass a lens of the image forming unit 130, and make a reflection image of the at least three markers 110 111 and 112 on an image sensor 133 integrated in the body portion 132. In other words, lights emitted from the markers 110 111 and 112 are transferred to the image forming unit 130 in two paths (first path: marker→image forming unit, second path: marker→reflector→image forming unit), and make two images (direct image and reflection image) of each of the markers 110 111 and 112 of the two paths (first and second paths).

As described above, when a direct image and reflection image are formed in the image forming unit 130, three-dimensional coordinates of the makers 110 111 and 112 are calculated (S130).

FIG. 5 shows a detailed process of calculating three-dimensional coordinates of each of the markers 110 111 and 112.

In order to calculate three-dimensional coordinates of the markers 110 111 and 112, first, two-dimensional coordinates of the direct image and reflection image of each of the markers 110 111 and 112 which are formed on the image forming unit 130 are calculated through the processor 140 (S131).

Herein, after calculating two-dimensional coordinates of the direct image and reflection image of each of the markers 110 111 and 112, a camera calibration is processed for each coordinates (S132).

As described above, after processing a camera calibration, three-dimensional coordinates of each of the markers 110 111 and 112 are calculated by using two-dimensional coordinates of the direct and reflection images (S133).

Referring to FIGS. 6 and 7, a detailed process of calculating three-dimensional coordinates of each of the markers 110 111 and 112 is described in below.

As shown in FIG. 6, one side of the image sensor 133 is virtually divided in a FOV (field of view) of a direct image and another side of the image sensor is virtually divided in a FOV (field of view) of a reflection image, two-dimensional coordinates of the direct image of the image sensor 133 is represented by a coordinate system (U,V), and two-dimensional coordinates of the reflection image of the image sensor 133 is represented by a coordinate system (U',V'). Referring to FIG. 7, a relationship between the two-dimensional coordinates of the markers 110 111 and 112 in real space and the three-dimensional coordinates of the markers 110 111 and 112 in real space may be represented in a formula below.

$$s \underbrace{\begin{bmatrix} u \\ v \\ 1 \end{bmatrix}}_{\tilde{m}} = \underbrace{\begin{bmatrix} \alpha & \gamma & u_0 \\ 0 & \beta & v_0 \\ 0 & 0 & 1 \end{bmatrix}}_{A} \underbrace{[r_1 \ r_2 \ r_3 \ t]}_{[x,t]} \underbrace{\begin{bmatrix} x \\ y \\ z \\ 1 \end{bmatrix}}_{\tilde{M}} \quad \text{[Formula 1]}$$

Herein, m is two dimensional coordinates of the markers in the image, M is three-dimensional coordinates of the markers in real space, and A(R, t) is a matrix of the camera In order to explain more briefly, when three-dimensional coordinates of real markers 110 111 and 112 are represented in X, a relational formula between three-dimensional coordinates of real markers 110 111 and 112 and coordinates of direct image ($x_L$), and a relational formula between three-dimensional coordinates of real markers 110 111 and 112 and coordinates of reflection image ($x_R$) are represented in below.

$$x_L = P_1 X$$

$$x_R = P_2 X \quad \text{[Formula 2]}$$

Herein, $P_1$ is a camera matrix of the direct image, and $P_2$ is a camera matrix of the reflection image.

And, relation formulas of the direct image and reflection image of each of the markers 110 111 and 112, $x_L = P_1 X$, $x_R = P_2 X$, may be represented in a linear equation AX=0, and the equation may be represented in Formula 3.

$$x(P^{3T}X) - (P^{1T}X) = 0$$

$$y(P^{3T}X) - (P^{2T}X) = 0$$

$$x(P^{2T}X) - y(P^{1T}X) = 0 \quad \text{[Formula 3]}$$

Herein, $P^{iT}$ is a row vector of the matrix P.

The formula 3 may be represented in Formula 4.

$$\begin{bmatrix} x_L P_1^{3T} - P_1^{1T} \\ y_L P_1^{3T} - P_1^{2T} \\ x_R P_2^{3T} - P_2^{1T} \\ y_R P_2^{3T} - P_2^{2T} \end{bmatrix} \begin{bmatrix} X \\ Y \\ Z \\ w \end{bmatrix} = [0] \quad \text{[Formula 4]}$$

Herein, W may be a scale factor.

Three-dimensional coordinates of the markers 110 111 and 112 are obtained by calculating X, Y, and Z through solving the linear equation represented in formula 4.

As described above, after calculating three-dimensional coordinates of each of the markers 110 111 and 112 through the processor 140, three-dimensional coordinates of the markers 110 111 and 112 in real space are compared to pre-stored geometric information of the markers which are adjacent to each other through the processor 140, and a spatial position and a direction of the markers 110 111 and 112 attached on the target 200 is calculated (S140).

Herein, as described above, geometric information between the adjacent markers 110 111 and 112 may be length information of straight lines L1 L2 and L3 which connect the marker adjacent to each other and angle information A1 A2 and A3 which are formed by the pair of straight lines coupling the markers 110 111 and 112 adjacent to each other.

In other words, the spatial position and the direction of the markers 110 111 and 112 are calculated by comparing the three-dimensional coordinates of the markers 110 111 and 112 in real space to length information of straight lines L1 L2 and L3 which connect the marker adjacent to each other and angle information A1 A2 and A3 which are formed by the pair of straight lines coupling the markers 110 111 and 112 adjacent to each other, in which the length information and the angle information are pre-stored in the processor 140.

As described above, a tracking system and method using the same according to an embodiment of the present invention, lights emitted from each of the markers 110 111 and 112 are directly flowed to an image forming unit 130 and a direct image is formed on the image forming unit 130 and, at the same time, lights reflected from the reflector 120 are flowed to the image forming unit 130 and a reflection image is formed on it. In other words, lights emitted from the markers 110 111 and 112 are transferred to the image forming unit 130 in two paths (first path: marker→image forming unit, second path: marker→reflector→image forming unit), and make two images (direct image and reflection image) of each of the markers 110 111 and 112 of the two paths (first and second paths).

Therefore, a tracking system and method using the same according to an embodiment of the present invention, one image forming unit 130 is used to calculate a spatial position and direction of the markers 110 111 and 120 attached on the target 200.

Therefore, there is an effect of reducing a manufacturing cost of the tracking system with small and lightweight, and relatively low restriction of surgical space comparing with conventional tracking system.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

The invention claimed is:

1. A tracking system comprising:
at least three markers attached on a target and emitting lights or reflecting lights emitted from at least one light source;
a reflector reflecting the lights which are emitted from the markers or the lights reflected by the markers;
an image forming unit which forms a direct image by directly receiving lights emitted from the markers and, at the same time, forms a reflection image by receiving lights reflected from the reflector after being emitted from the markers; and
a processor which calculates three-dimensional coordinates of the markers using the direct image and the reflection image formed on the image forming unit, and calculates a spatial position and direction of the target by comparing the three-dimensional coordinates of the markers with a pre-stored geometric information between the markers adjacent to each other.

2. The tracking system of claim 1, wherein the reflector is a mirror which reflects lights emitted from the markers towards the image forming unit to form a reflection image.

3. The tracking system of claim 1, wherein the reflector is positioned on a same optical path as the image forming unit, and changes an image forming position of the reflection image by changing at least one of an installation position, an angle, and a shape of a reflection surface under the control of the processor.

4. The tracking system of claim 1, wherein the image forming unit is a camera which forms an image by receiving the light emitted from the markers and the lights reflected from the reflector.

5. The tracking system of claim 1, wherein the geometric information between the markers comprises length information of straight lines which connect the markers adjacent to each other, and angle information which is formed by a pair of straight lines adjacent to each other.

6. A tracking method comprising:
forming a direct image on a n image forming unit by directly receiving lights emitted from at least three markers attached on a target and, at the same time, forming a reflection image by receiving lights reflected from a reflector that is installed in a specific area to reflect lights emitted from the markers;
calculating three-dimensional coordinates of each of the markers through a processor by using the direct image and reflection image of the markers formed on an image forming unit; and
calculating a spatial position and a direction of the target by comparing the three-dimensional coordinates of each of the markers and geometric information between the markers adjacent to each other, wherein the geometric information is pre-stored in the processor.

7. The tracking method of claim 6, wherein the geometric information comprises length information of straight lines which couple the marker adjacent to each other and angle information which is formed by the pair of straight lines adjacent to each other.

8. The tracking method of claim 6, wherein forming the reflection image on the image forming unit comprises controlling at least one of an installation position, an angle, and a shape of a reflection portion of the reflector through the processor to change an image forming position of the reflection image on a same optical path.

9. The tracking method of claim 6, wherein calculating the three-dimensional coordinates of the markers comprises calculating two-dimensional coordinates of the direct and reflection images of the markers through the processor; and
calculating the three-dimensional coordinates of the markers through the processor by using the two-dimensional coordinates of the direct and reflection images of the markers.

* * * * *